United States Patent [19]

Kohayakawa

[11] 4,452,517
[45] Jun. 5, 1984

[54] FOCUSING SYSTEM FOR EYE-GROUND CAMERA

[75] Inventor: Yoshimi Kohayakawa, Yokohama, Japan

[73] Assignee: Canon Kabushiki Kaisha, Tokyo, Japan

[21] Appl. No.: 346,870

[22] Filed: Feb. 8, 1982

Related U.S. Application Data

[63] Continuation of Ser. No. 109,275, Jan. 3, 1980, abandoned.

[30] Foreign Application Priority Data

Jan. 16, 1979 [JP] Japan .................................. 54-3734
Jan. 19, 1979 [JP] Japan .................................. 54-5177

[51] Int. Cl.³ .......................... A61B 3/14; G03B 29/00
[52] U.S. Cl. ......................................... 351/206; 354/62
[58] Field of Search ................... 351/206, 207, 208; 354/62

[56] References Cited

U.S. PATENT DOCUMENTS

| | | |
|---|---|---|
| 3,016,000 | 1/1962 | Noyori . |
| 3,614,214 | 10/1971 | Cornsweet et al. . |
| 3,925,793 | 12/1975 | Matsumura et al. . |
| 3,936,844 | 2/1976 | Matsumura .................... 351/206 |
| 4,149,787 | 4/1979 | Kobayshi ...................... 351/206 |
| 4,208,107 | 6/1980 | Oharek ......................... 351/206 |

*Primary Examiner*—John K. Corbin
*Assistant Examiner*—Rodney B. Bovernick
*Attorney, Agent, or Firm*—Fitzpatrick, Cella, Harper & Scinto

[57] ABSTRACT

The focusing system of the present invention includes an objective lens facing an eye to be examined, an aperture mirror for reflecting the illuminating light, an aperture stop, a photographing lens, a photosensitive lens and a focusing lens provided between said aperture stop and the photographing lens.

The system further comprises a system for directing the beam reflected at the reflecting spot located at the image side of the objective lens or by the aperture mirror or a dichroic mirror located at the image side of the aperture mirror toward the eye ground, and a light-receiving optical system for focusing the beam reflected from the eye ground onto a photosensor through the objective lens, wherein the focusing lens is driven by the output of said photosensor.

29 Claims, 16 Drawing Figures

FOCUSING SYSTEM FOR EYE-GROUND CAMERA

This is a continuation of application Ser. No. 109,275, filed Jan. 3, 1980, now abandoned.

BACKGROUND OF THE INVENTION

1. Field of the Invention

The present invention relates to an eye examining instrument, and more particularly to a system for focusing the instrument to the ground of the eye to be examined.

2. Description of the Prior Arts

In a conventional eye-ground camera, the focusing to the eye ground has been achieved by adapting the sight of the eye to cross-hairs in the finder and by adjusting the photographing lens in such a manner that the eye ground can be clearly viewed in this state. However such focusing method inevitably involves personal fluctuation and is difficult to conduct rapidly.

U.S. Pat. No. 3,016,000 discloses a method of focusing the camera to the eye ground by projecting a focus mark onto the eye ground and adjusting the focusing lens so as that the focus mark can be clearly viewed. Also U.S. Pat. No. 3,925,793 (German Pat. No. 2,415,319) and U.S. patent application Ser. No. 945,845 disclose a focusing method wherein plural marks are projected on the eye ground and the marks are aligning under observation. Although rapid focusing has been rendered possible by these methods, there still remains a strong demand for automatic focusing of the camera, as the setting of an eye-ground camera simultaneously requires the alignment of the eye axis with the optical axis of the objective lens, the distance adjustment between the cornea and the objective lens, and the focus adjustment. The operator has to constantly pay attention to these three factors as the above-mentioned alignment and distance are easily affected by small movements of the subject to be examined while the focusing is affected by a change in the sight of the eye to be examined. For this reason automatic focusing, if realized, will significantly alleviate the load to the operator and contribute to the probability of obtaining photographs of improved image quality. Also in case of continuous photographing with successively displaced viewing fields, it becomes necessary to correct the focusing for each field displacement, and an automatic focusing will contribute to the image quality in such case.

A pioneer invention for automatic focusing of the eye-ground camera to the eye ground is disclosed in U.S. Pat. No. 3,614,214, in which a dichroic mirror reflecting the infrared light but transmitting the visible light is provided in front of an ordinary eye-ground camera in an oblique position to deflect the detecting beam from an automatic optometer toward the eye to be examined and to again deflect the reflected beam from the eye to said optometer, whereby the focusing lens of the eye-ground camera is adjusted by the output of said optometer. In case, however, of adopting a wider photographing angle there is required a shorter working distance between the camera and the eye, and the presence of the dichroic mirror in front of the camera will hinder the use of a wider photographing angle. Also the increased diameter of the photographing beam required in case of a wider photographing angle requires a longer dichroic mirror, thus leading to a drawback of an increased working distance between the eye and the camera.

The above-mentioned method is advantageous in that the focusing can be achieved without the artificial mydriasis induced by the use of a mydriatic as said optometer utilizes, as the detecting beam, an infrared light not reactive to the pupil. However, the determination of the photographing field, which is required in addition to the focusing in the eye-ground photographing, cannot be achieved by projecting an illuminating light in the infrared wavelength region from the eye-ground camera since it is deflected by said dichroic mirror and does not reach the eye to be examined.

In addition, the use of this eye ground camera is characterized by difficulties specific thereto since the illumination of the eye ground and the observation of the reflected beam occur through the small aperture of the pupil, and a part of the illuminating beam may be reflected by the cornea of the eye to be examined.

SUMMARY OF THE INVENTION

The principal object of the present invention is to provide a system capable of automatically focusing the eye-ground camera to the eye ground to be examined.

Another object of the present invention is to provide a system allowing the use of a shorter working distance, thereby enabling an enlarged image angle.

Still another object of the present invention is to provide a system allowing the observation of the eye ground even during the focusing operation.

Still another object of the present invention is to provide a system having a faster focusing response speed. In the preferred embodiments this object is achieved by the use of a lighter focusing lens, particularly of a smaller diameter realized by positioning the focusing lens adjacent to the photographing aperture stop. Also such structure of the focusing lens positioned adjacent to the aperture stop allows reduction of the displacement of the conjugate image of the aperture stop resulting from the displacement of the focusing lens, thereby achieving an improvement in the accuracy of focus detection.

Still another object of the present invention is to satisfactorily adapt the focus detecting system into the optical system of the eye-ground camera.

In the following first, second, fourth and fifth preferred embodiments, an oblique ray emitted from a position on the optical axis or a corresponding position is projected onto the eye ground through a projection optical system and the ray reflected from the eye ground is received by a photosensor, whereby, in response to the output of said photosensor, the projection optical system is adjusted so that the reflected ray falls on a position on the optical axis or on a corresponding position on the photosensor, or the focusing lens is displaced by an amount corresponding to the distance between the entrance point of the reflected ray and the optical axis.

Also in the sixth preferred embodiment double images of the eye ground, for example of a blood vessel, are projected on a photosensor array and the focusing lens is adjusted according to the distance of said double images.

DESCRIPTION OF THE PREFERRED EMBODIMENTS

Figure 1:
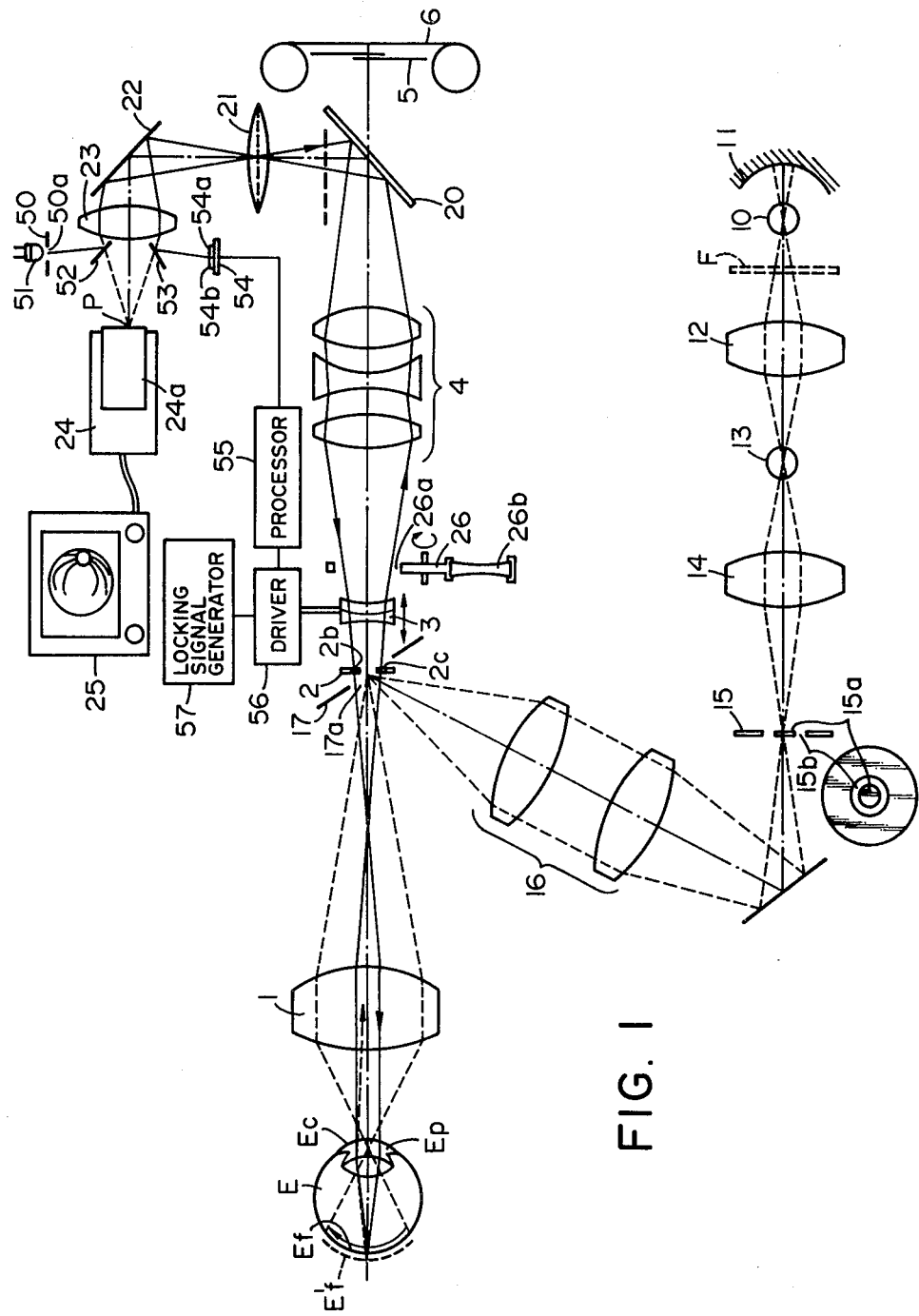
FIG. 1 is a cross-sectional view of a first embodiment of the present invention.

In FIG. 1 showing a first embodiment of the present invention, there is illustrated a human eyeball E wherein Ef, Ec and Ep respectively represent the eye ground, cornea and pupil. A photographing system is composed of an objective lens 1, a photographing aperture stop 2, a negative focusing lens 3, a photographing lens 4, a shutter 5 and a photographic film 6, wherein the objective lens 1 forms an intermediate image of the eye ground which is again focused on the photographic film 6 by means of the focusing lens 3 and the photographing lens 4.

Also there are shown an observation light source 10 such as a tungsten lamp, a reflector 11, a condenser lens 12, a photographing light source 13 such as a strobo light tube, a second condenser lens 14, and a ring slit plate 15 having an annular aperture 15b around a central shield circle 15a. Said light sources 10 and 13 are provided in mutually conjugate positions with respect to the first condenser lens 12, and the light source 13 and the ring slit plate 15 are provided in mutually conjugate positions with respect to the second condenser lens 14. There are also shown a relay lens 16 and an apertured mirror 17 having an aperture of a dimension not hindering the beam entering the aperture stop 2. Said apertured mirror 17 is located in such a manner as to be conjugate with said ring slit plate 15 with respect to the relay lens 16 and in such a manner that the image of the ring slit plate formed by the beam reflected by said apertured mirror 17 through the objective lens 1 is conjugate with the aperture stop 2 with respect to said objective lens 1. Also it is designed in such a manner that the image of the ring slit plate at an appropriate working distance coincides with the position of a frontal part of the eyeball, for example the pupil Ep. The foregoing components 10 to 17 and the objective lens 1 constitute an illuminating system.

Further there are shown a quick return mirror 20, a field lens 21 positioned in conjugate relationship with the photographic film 6 with respect to said mirror 20, a deflecting mirror 22, an imaging lens 23, a television camera 24 with an imaging tube 24a, and a television receiver 25. The imaging lens 23 focuses a space image on the field lens 21 again onto a photosensitive face of the imaging tube 24a.

A turret 26 is provided for sight correction which is normally positioned so as to insert a lensless portion 26a thereof into the photographing system but can be rotated to insert a correcting lens 26b into the optical path in case the subject to be examined has a strong abnormality in his or her sight.

The foregoing explanation provides the basic structure of an eye-ground camera with observation through a television system, which can also be modified to an eye-ground camera without the use of a mydriatic by inserting a filter F in front of the observing light source 10 for transmitting the infrared and near-infrared light while intercepting the visible light and using an imaging tube 24a sensitive to such infrared and near-infrared light, or to an ordinary eye-ground camera by guiding the light beam reflected by the mirror 22 to an unrepresented eyepiece.

In the present embodiment, the focusing lens 3 is positioned as close as possible to the aperture stop 2 to reduce the lens diameter, and is designed to have a focal length larger than that of the photographing lens 4. The photographing lens 4 is of such a structure and such a number of lens elements as to correct the aberrations within said lens, and the lens for sight correction is provided between the focusing lens 3 and the photographing lens 4 to enable said focusing lens to be positioned close to the aperture stop.

Figure 2:
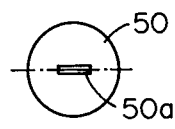
FIG. 2 and 3 are plan views of components used therein.

A mask 50 has a rectangular aperture 50a of a shape shown in a plan view in FIG. 2 and is positioned in such a manner that the longer side of the aperture is perpendicular to the plane of the paper bearing FIG. 1, and the center of said aperture 50a is positioned symmetrical to the crossing point P of the optical axis and the imaging tube 24a with respect to a mirror 52. There are also shown an illuminating light source 51 comprising of an infrared light-emitting diode in the present embodiment, spot mirrors 52 and 53, a photoelectric transducer 54 having two elements 54a and 54b divided by a boundary which is perpendicular to the plane of the paper bearing FIG. 1 and positioned symmetrical to said point P with respect to the spot mirror 53, an electric processing circuit 55 for generating an electric signal indicating the direction of desired displacement of the focusing lens 3 until the difference between the outputs of said elements 54a and 54b becomes zero, a driver 56 for example incorporating a servo motor coupled with the focusing lens 3 to axially displace the same in response to the output from said processing circuit 55, and a locking signal generator 57 for locking the lens 3 at the shutter release in order to prevent the erroneous function of the driver 56.

Figure 3:
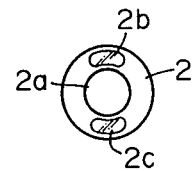

The aforementioned aperture stop 2 in the present embodiment has a structure as shown in a plan view in FIG. 3, wherein there are provided, in addition to the aperture 2a, additional small apertures 2b and 2c positioned above and below said aperture 2a and provided with filters for transmitting the infrared light and interrupting the visible light, said apertures 2b and 2c being positioned in conjugate relationship with the image of the ring slit plate formed on the pupil Ep. Also the aforementioned spot mirrors 52 and 53 are positioned in conjugate relationship with said image with respect to the imaging lens 23, mirror 22, field lens 21, quick return mirror 20, photographing lens 4, focusing lens 3 and objective lens 1 in the relaying optical system, so that said small apertures 2b and 2c are conjugate with said spot mirrors 52 and 53.

On the other hand the mask 50 and the photosensitive face of the transducer 54 are respectively in conjugate relationship with the eye ground in the focused state with respect to said spot mirror 52 or 53 and also to the above-mentioned relaying optical system.

The above-explained embodiment functions in the following manner. An oblique infrared beam emitted from the mask aperture 50a illuminated by the infrared light-emitting diode 51 is reflected by the spot mirror 52, then converged by the imaging lens 23, reflected by the mirror 22, focused on and transmitted by the field lens 21, again reflected by the quick return mirror 20, then focused through the photographing lens 4, focusing lens 3 and the filtered small aperture 2b, and emitted by the objective lens 1 in an approximately collimated state toward the eye E to be examined to form an image of the mask aperture 50a on the eye ground. The beam diffuse reflected by the eye ground and passing through an area of the pupil conjugate with the small aperture 2c is emitted from the eye E in an approxmately collimated state, then focused by the objective lens 1 on a plane conjugate with the eye ground with respect to said lens 1, then transmitted through the filtered small aperture 2c, again focused on the field lens 21 through the focusing lens 3, photographing lens 4 and quick return mirror 20, and finally focused on the photoelectric transducer 54 through the mirror 22, imaging lens 23 and spot mirror 53.

If the photographing system is focused to the eye ground Ef, the image of the mask aperture 50a is formed on the axial position on the eye ground, so that the reflected image of said aperture is formed on the axial position, i.e. on the boundary of two elements, of said photoelectric transducer 54.

Figure 4:
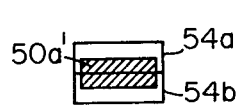
FIGS. 4 and 5 are plan views both showing the relation between the image of an aperture and the photosensor element.

FIG. 4 shows this state, wherein 54a and 54b are the photoelectric elements shown in FIG. 1 while 50a' is the reflected image of the mask aperture. When said reflected image is equally divided between two elements as shown in FIG. 4, said elements 54a and 54b provide mutually equal signals so that the processing circuit 55 does not release a difference signal to maintain the focusing lens 3 in a stationary state.

Figure 5:
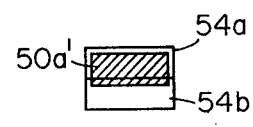

On the other hand, in case the eye to be examined has a stronger refractive force, the beam forming the image of the mask aperture is focused in front of the eye ground Ef, as if the eye ground is retracted backward to the broken-lined position E'f in FIG. 1. As the beam forming the image of the mask aperture is oblique to the optical axis, said image on the eye ground E'f becomes somewhat blurred and simultaneously displaced upwardly, whereby the reflected image 54'a of the mask aperture on the photoelectric transducer 54 is likewise displaced as shown in FIG. 5. Also in case of a weaker refractive force of the eye, the behavior of the system is as if the eye ground is displaced forwardly so that the reflected image of the mask aperture is displaced in a direction opposite to that in the foregoing case.

In such circumstances the photoelectric elements 54a and 54b receive mutually unbalanced lights to provide mutually different signals, thus indicating the direction of effective displacement of the eye ground and corresponding displacement of the image of the mask, The processing circuit 55 utilizes this indicator to activate the driver 56 to thereby displace the focusing lens 3 in a determined direction. Said displacement of the focusing lens 3 causes the displacement of the image of mask aperture 50a formed on the eye ground Ef, thus similarly displacing the reflected image on the photoelectric transducer 54. When said image becomes equally divided between the two elements thereof, the circuit 55 terminates the output signal thereof, whereby the driver 56 secures the focusing lens 3 in the adjusted, focus position. In this manner the photographing or observing system can be focused to human eyes having different refractive power, and the focusing is constantly corrected by the focusing lens 3 even in case the sight of the subject to be examined changes during the observation.

In the present embodiment, as the eye ground is constantly maintained in focus, the operator, while observing the screen of the television receiver 25, can actuate the shutter button at an appropriate timing to displace the quick return mirror 20, activate the light source 13 and open the shutter 5 to complete the photographing.

In the foregoing embodiment the focusing lens 3 is positioned close to the photographing aperture stop while a fixed lens is positioned close to the photographic film in order to minimize the displacement of the conjugate image of said aperture stop thereby suppressing the influence of vignetting by the aperture stop.

Figure 6:
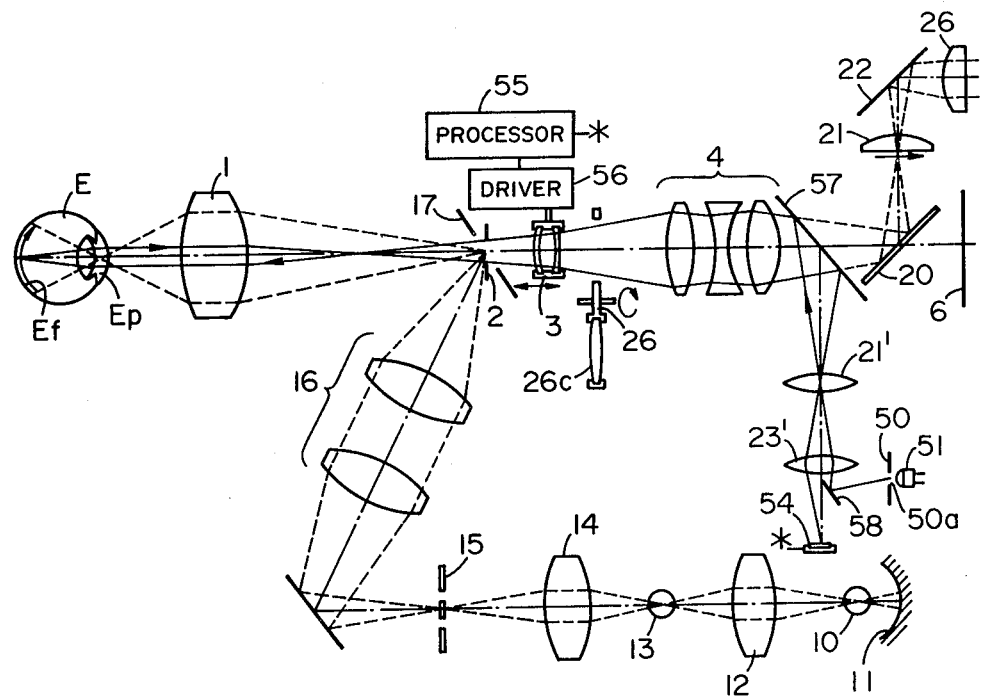
FIG. 6 is a cross-sectional view of a second embodiment of the present invention.

FIG. 6 shows a second embodiment of the present invention, wherein the same components as those in FIG. 1 are represented by the same numbers. In said second embodiment there are provided an eyepiece 26 capable of certain adjustment according to the sight of the operator and positioned in front of the mirror 22, an oblique mirror 57 positioned between the photographing lens 4 and the quick return mirror 20 and capable of transmitting the visible light and intercepting the infrared light by means of multiple interference layers, a field lens 21' placed in a conjugate position with the photographic film with respect to the mirror 57, an imaging lens 23', an oblique mirror 58 covering a half of the optical path and positioned in conjugate relationship with the pupil Ep with respect to the imaging lens 23', field lens 21', infrared-reflecting mirror 57, photographing lens 4, focusing lens 3 and objective lens 1. In the present embodiment the focusing lens 3 is provided with a negative focal length and is composed of two separate lens elements. In the aboveexplained structure, the beam emitted by the aperture 50a illuminated by the light source 51 is reflected by an oblique mirror 58, then focused by the imaging lens 23' to form an image of said aperture on the field lens 21', again reflected by the infrared-reflecting mirror 57, then transmitted by the photographing lens 4 and the focusing lens 3 to again form an image between the aperture stop 2 and the objective lens 1, and introduced through said objective lens 1 into the eye E to be examined to form an image of the mask aperture 50a on the eye ground Ef.

The beam reflected by the eye ground is emitted from the eye, then inversely transmitted through the above-explained light path and focused by the imaging lens 23' on the photoelectric transducer 54. The displacement of the image of said aperture and of the focusing lens is achieved in the same manner as explained in the foregoing embodiment shown in FIG. 1.

Figure 7:
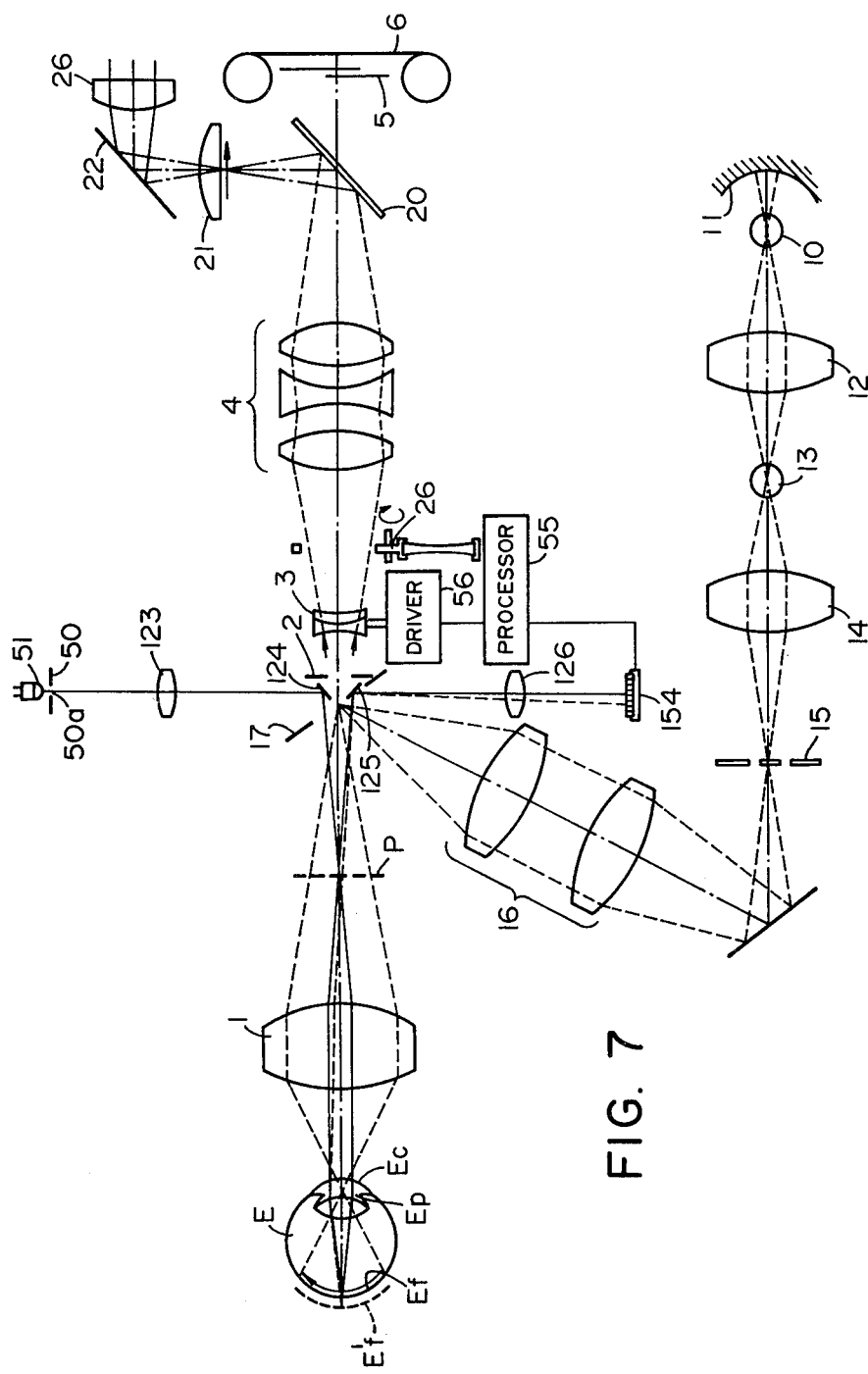
FIG. 7 is a cross-sectional view of a third embodiment of the present invention.
Figure 8:
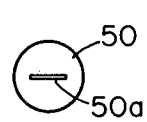
FIGS. 8 and 9 are plan views of components used therein.
Figure 9:

FIG. 7 shows a third embodiment of the present invention. The new components not appearing in the foregoing embodiments, include a projection lens 123 for forming an image of a linear slit 50a as shown in FIG. 8 on a plane P conjugate with the eye ground of a normal eye with respect to the objective lens 1, small oblique mirrors 124 and 125 which are placed outside the aperture of the aperture stop 2 as shown in a front view in FIG. 9 and are positioned in conjugate relationship with the eye pupil Ep (wherein the image of the ring slit plate 15 is formed) with respect to the objective lens 1, a light-receiving lens 126, and a photosensor array 154 which is preferably composed of a self-scanning solid-state image sensor such as a charge-coupled device and is placed in conjugate relationship with said plane P with respect to said light-receiving lens 126.

In the above-explained structure, the infrared beam emitted by the slit 50a illuminated from an infrared light-emitting diode constituting the light source 51 is focused by the projection lens 123 onto said plane P after reflection by the mirror 124, then emitted by the objective lens 1 in a collimated state and introduced into the eye E to be examined to form an image on the eye ground Ef. As the image-forming beam is oblique to the optical axis because of the off-axis position of the small mirror 124, said image of the slit 50a is formed in the axial position in case of a normal eye but is displaced upwardly or downwardly in case of an abnormality in the sight of said eye.

The diffuse reflected beam from the eye ground Ef is introduced into the objective lens 1, focused on said conjugate plane P, then reflected by the small mirror 125 and focused by the light-receiving lens 126 to form a reflected image of the slit 50a on the photosensor array 154.

Figure 10:
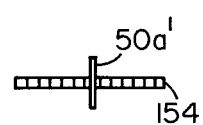
FIG. 10 is a plan view showing the relation between the slit image and the photosensor array.

FIG. 10 is a magnified view of said array wherein each section represents an independent photosensor element. The central section, for example of said array 154 corresponds to the position of the reflected image of the slit in case of a normal eye, while said image becomes displaced from said position if the eye has a positive or negative abnormality in the sight thereof.

When the image of the slit is formed on the central element of the array 154 as explained above, the processing circuit 55, identifying such position, generates a signal indicating the position of the focusing lens 3 optimum for focusing the photographing system to the eye ground Ef, thus activating the driver 56 and accordingly displacing the focusing lens 3 to said position.

In case of a near-sighted eye having a stronger refractive power, the slit image is formed in a position closer to the lens of the eye as if the eye ground is retracted to a broken-lined position E'f. Consequently the image-forming beam is reflected at a position located above the optical axis as represented by the broken line, thus causing a displacement of the slit image on the photosensor array 154. Although the slit image on said array becomes out of focus in this case, the accuracy of the measurement is not affected by such out-of-focus state since the measurement solely depends on the detection of the central position of said slit image.

Thus the processing circuit 55 similarly generates a signal indicating the position of the focusing lens 3, and the driver 56 in response to this signal, then displaces said lens 3 to the focused position.

In contrast to the foregoing first embodiment in which the position of the focusing lens is constantly servo controlled so as to maintain the photographing system in focus to the eye ground, it is also possible in the present embodiment to adopt a structure in which the focusing lens is adjusted to the desired position immediately before the shutter release. This is due to a fact that, in contrast to the first embodiment utilizing the observation on a television receiver of which image is extremely difficult to observe unless it is constantly maintained in focus, the direct viewing through an eye-piece allows satisfactory observation of the eye ground only with certain adjustment of the eye-piece since the eye function of the operator contributes to compensate such out-of-focus state.

Figure 11:
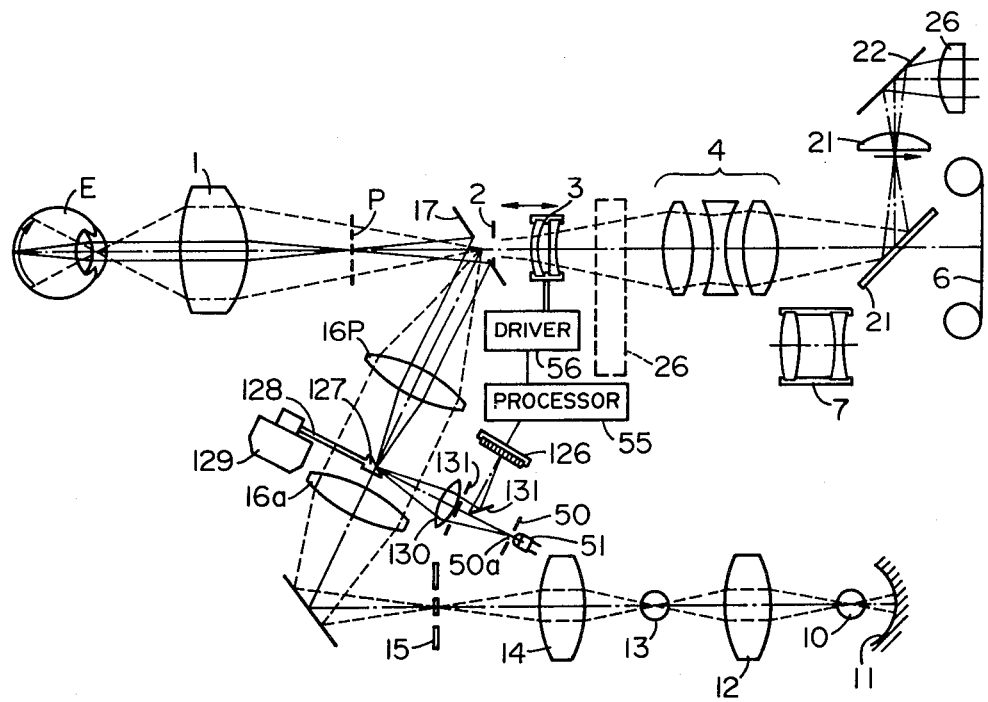
FIG. 11 is a cross-sectional view of a fourth embodiment of the present invention.
Figure 12:
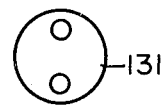
FIG. 12 is a plan view showing a component used therein.

FIG. 11 shows a fourth embodiment of the present invention where an apertured mirror 17 rather than two small mirrors, is used to project the image of the slit 50a and for detecting the reflected image. In FIG. 11 there are shown a spot mirror 127 mounted on an end of a lever 128 and normally obliquely inserted in the optical path but retracted therefrom at the photographing operation by means of a rotary solenoid 129, a relay lens 130, a two-apertured stop 131 having two apertures as shown in FIG. 12 and positioned in conjugate relationship with the image of the ring slit plate 15 formed on the pupil Ep with respect to the relay lens 131, a part 16P of relay lens, apertured mirror 17 and objective lens 1, and an oblique mirror 131. The slit mask 50 is positioned in conjugate relationship with a plane P, which is in turn conjugate with the eye ground, with respect to the relay lens 130, spot mirror 127, the part 16P of the relay lens and apertured mirror 17, while the photosensitive face of the photosensor array 126 is also conjugate with said plane P.

An afocal converter 7 capable of modifying the focal length of the photographing system may be inserted behind the photographing lens 4.

Figure 13:
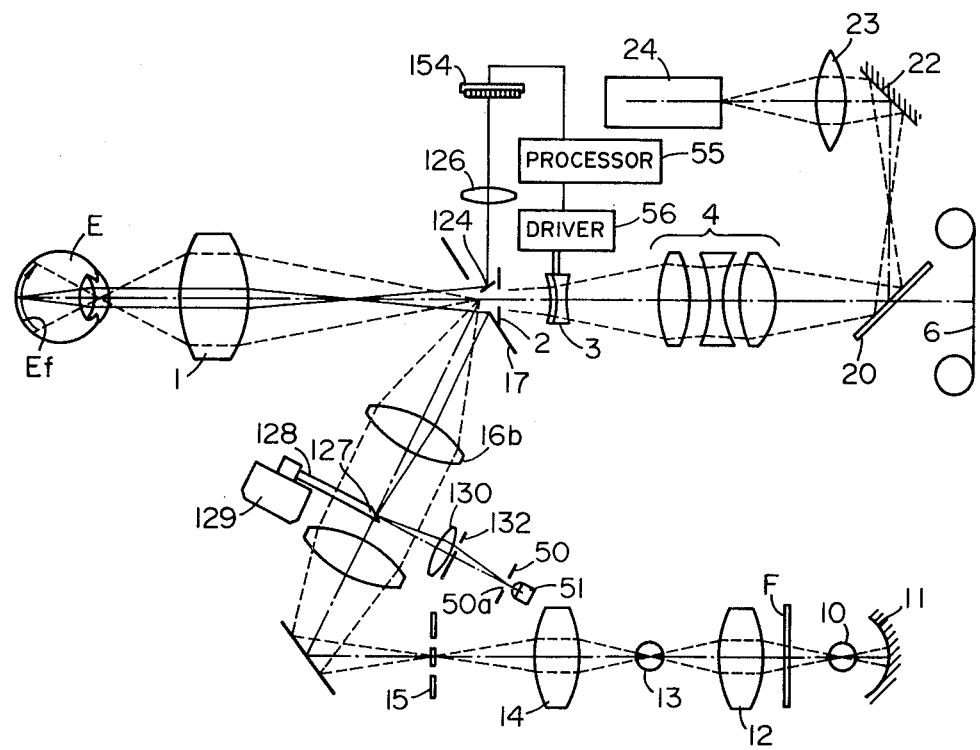
FIG. 13 is a cross-sectional view of a fifth embodiment of the present invention.
Figure 14:
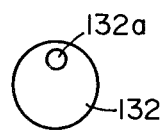
FIG. 14 is a plan view showing a component used therein.

FIG. 13 shows a fifth embodiment of the present invention, wherein the image projection is achieved through an apertured mirror 17 while the beam detection is achieved through a small mirror 124. An eccentrically apertured stop 132, of a shape shown in FIG. 14, is positioned in conjugate relationship with the image of the ring slit plate 15 formed on the pupil with respect to the relay lens 130, spot mirror 127, a part 16b of the relay lens, apertured mirror 17 and objective lens 1, while the small mirror 124 is positioned also in conjugate relationship with said image with respect to the objective lens 1. Also the slit mask 50 and the array 154 are respectively in conjugate relationship with the eye ground Ef with respect to the respective relaying optical system.

In the above-explained structure, the beam emitted from the slit 50a illuminated by the light source 51 is guided through the eccentric aperture 132a of the apertured plate 132, then focused by the relay lens 130 onto the spot mirror 127, then again focused by a part 16b of the relay lens after reflection by the apertured mirror 17 and guided to the eye E from the objective lens 1 in a collimated state. The reflected beam from the eye ground is focused by the objective lens 1, and again focused through the small mirror 124 and the light-receiving lens 126 onto the array 154. Also in the present embodiment, as the position of the reflected image of the slit 50a on the array 154 depends on the refractive power of the eye, it is possible to adjust the axial position of the focusing lens 3 according to the position of said slit image.

Figure 15:
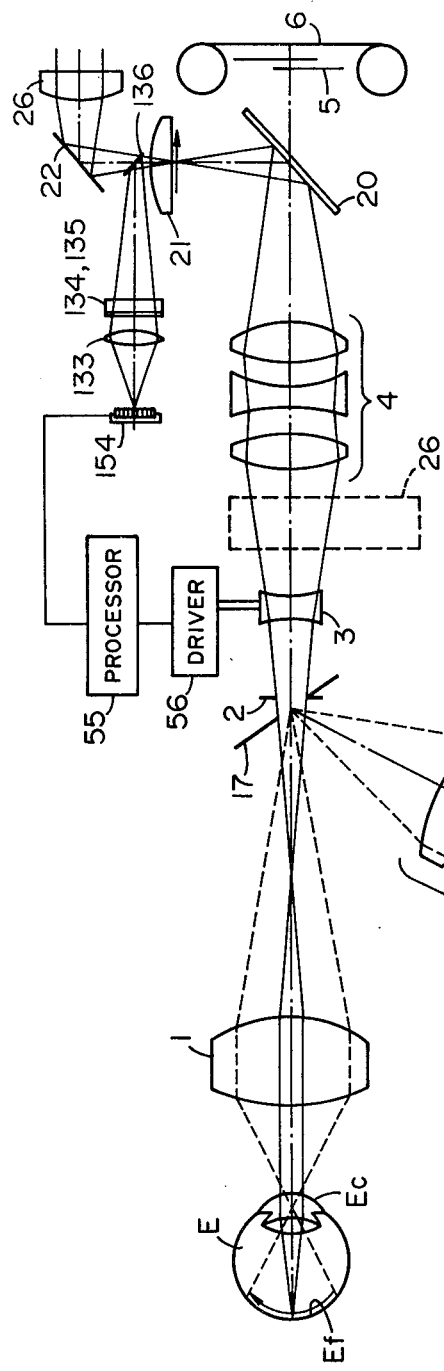
FIG. 15 is a cross-sectional view of a sixth embodiment of the present invention.
Figure 16:
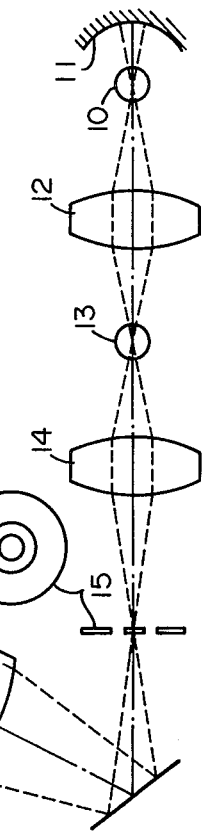
FIG. 16 is a plan view showing a part of the structure of said sixth embodiment.
Figure 16:
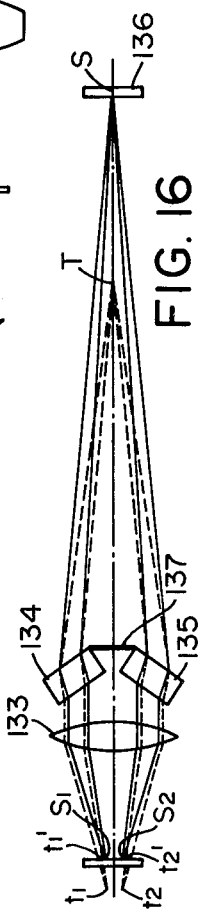

In contrast to the foregoing embodiments wherein a mark is projected onto the eye ground and the refractive power of the eye is determined by the position of the reflected image of said mark on a photosensor to in turn focus a photographing system, the following sixth embodiment utilizes the displacement of an image of the eye ground resulting from an abnormality in the sight of the eye to be examined. Referring to FIG. 15, there are shown an imaging lens 133, parallel-faced flat plates 134 and 135 positioned inversely obliquely to the optical axis, a semi-transparent mirror 136 positioned in the vicinity of the field lens, and a light shield 137. The elements 133 to 136 and the array 154 are positioned as shown in plan view in FIG. 16. In case of a normal eye, an axial area of the eye ground thereof forms an image S on the semi-transparent mirror 136, and the beam emitted from said image S is refracted by said flat plates 134 and 135 to form displaced images S1 and S2 on the photosensor array 154. The distance between said images S1 and S2 is memorized as corresponding to a normal eye. Then in case of another subject having a different sight, the image S is displaced to another position T, whereby the imaging lens 133 forms corresponding images at the positions t1 and t2. Consequently the photosensor array detects the centers t1' and t2' of the converging beams, the distance between which is utilized to identify the sight of the subject to be tested and to adjust the position of the focusing lens.

As explained in the foregoing, the present invention allows simplification of the drive mechanism as the focusing lens alone is all that is required to be moved. Rapid focusing operation is also achieved by the use of a lighter and smaller focusing lens. It is also effective to employ a plastic lens as the focusing lens in order to reduce the weight thereof.

What I claim:

1. An eye examining instrument comprising:
    a photographing system comprising objective means mounted to face an eye to be examined, an aperture stop, movable lens means, fixed lens means and image detecting means in succession;
    an illumination system coupled to said photographing system for illuminating the ground of said eye;
    an observing system coupled to said photographing system for observing said ground of said eye;
    reflection means positioned on the image side of said objective means for transmitting a light beam to said ground of said eye for observation;
    photosensing means for generating an output signal related to the position of a light beam incident thereon relative to an expected positioned;
    a light receiving system for directing a light beam transmitted from said reflection means and reflected from said ground of said eye onto said photosensing means;
    said movable lens being movable to simultaneously focus the image of a portion of said eye on said image detecting means and to focus said light beam, directed by said light receiving system, on said expected position of said photosensing means; and
    drive means for displacing said movable lens means in response to the output signal generated by said photosensing means until said image is focused on said image detecting means.

2. An eye examining instrument according to claim 1, further comprising a mark projection system for projecting a marking beam through said objective means in such a manner that the central ray of said marking beam is oblique to the optical axis of the eye to be examined.

3. An eye examining instrument according to claim 2, wherein the energy source of said marking beam is positioned on the optical axis of said mark projection system.

4. An eye examining instrument according to claim 2, wherein the energy source of said marking beam is positioned on a point equivalent to a point on the optical axis of said mark projection system.

5. An eye examining instrument according to claim 2, wherein said mark projection system is adapted to be focused to the eye ground of the eye to be examined.

6. An eye examining instrument according to claim 1, wherein said photosensing means comprises two adjacent photocells the boundary between which lies on the optical axis of said light receiving system.

7. An eye examining instrument according to claim 1, wherein said photosensing means is a photosensor array.

8. An eye examining instrument according to claim 1, wherein said light beam as transmitted from said reflection means and reflected from said ground of said eye is transmitted by said movable lens means.

9. An eye examining instrument comprising:
    a photographing system comprising objective means mounted to face an eye to be examined, an aperture stop and focusing means for focusing an image on an image plane;
    an illumination system coupled to said photographing system for illuminating the ground of said eye;
    a mark projection system for projecting a marking beam through said objective means to said ground of said eye, to be reflected therefrom, in such a manner that the central ray of said marking beam is oblique to the optical axis of said eye;
    photosensing means for generating an output signal related to the position of a marking beam incident thereon relative to an expected position;
    a light receiving optical system for directing the marking beam reflected by said ground of said eye through said objective means onto said photosensing means; said focusing means being adjustable to simultaneously focus the image of said ground of said eye on said image plane and to focus said marking beam, directed by said light receiving optical system, on said expected position of said photosensing means; and
    drive means for adjusting said focusing means in response to the output signal generated by said photosensing means until said image is focused on said image plane.

10. An eye examining instrument according to claim 9, wherein said mark projection system comprises beam limiting means mounted at a position substantially conjugate with the pupil of the eye to be examined.

11. An eye examining instrument according to claim 10, wherein said beam limiting means is a spot mirror.

12. An eye examining instrument according to claim 10, wherein said beam limiting means is a diaphragm.

13. An eye examining instrument according to claim 9, wherein said light receiving optical system comprises beam limiting means mounted at a position substantially conjugate with the pupil of the eye to be examined.

14. An eye examining instrument according to claim 13, wherein said beam limiting means is a spot mirror.

15. An eye examining instrument according to claim 13, wherein said beam limiting means is a diaphragm.

16. An eye examining instrument according to claim 9, wherein said mark projection system is focused to project said marking beam to said ground of said eye simultaneously with focusing of said photographing system.

17. An eye examining instrument according to claim 9, wherein said light receiving optical system is focused to direct said marking beam to said expected position on said photosensing means simultaneously with focusing of said photgraphing system.

18. An eye examining instrument according to claim 9, wherein said marking beam as both projected from said mark projecting system and reflected from said ground of said eye is transmitted by said focusing means.

19. An eye examining instrument comprising:
a photographing system comprising objective means mounted to face an eye to be examined, an aperture stop, and focusing means for focusing an image on an image plane;
an illumination system coupled to said photographing system for illuminating the ground of said eye;
reflection means positioned on the image side of said focusing means for transmitting a beam of light to said ground of said eye;
a photosensor array for generating an output signal related to the position of a light beam incident thereon relative to an expected position;
a light transmitting optical system for guiding a light beam transmitted by said reflection means to said ground of said eye and reflected therefrom to said photosensor array; said focusing means being adjustable to simultaneously focus the image of said ground of said eye on said image plane and to focus said light beam, guided by said light transmitting optical system, on said expected position of said photosensor array; and
drive means for adjusting said focusing means in response to the output signal generated by said photosensor array until said image is focused on said image plane.

20. An eye examining instrument according to claim 19, further comprising light beam splitting means for splitting said light beam guided by said light transmitting optical system into two light beams and refracting the split light beams in front of said photosensor array.

21. An eye examining instrument according to claim 20, wherein said focusing means is adjustable to simultaneously focus the image of said ground of said eye on said image plane and to focus each of said two light beams on a different expected position on said photosensor array and wherein said output signal is related to the distance between the positions of said light beams on said photosensor array relative to the distance between said expected positions thereof.

22. An eye examining instrument comprising:
a photographing system including front optical means adapted to face an eye to be examined, a diaphragm, optical path dividing means arranged on the main optical path on the front optical means side for dividing the optical path into first and second auxiliary optical paths, image detecting means arranged on said first auxiliary optical path for detecting the image of the ground of the eye being examined and focusing means for focusing said photographing system;
an illumination system coupled to said photographing system for illuminating the ground of the eye;
an observing system coupled to said photographing system for observing the ground of the eye;
photosensing means arranged on said second auxiliary optical path for sensing a pattern of energy reflected from the ground of the eye and generating electric information; and
actuating means for actuating said focusing means in response to the electrical information generated by said photosensing means until said photographing system is focused on the ground of the eye.

23. An instrument according to claim 22, further comprising a mark projection system for projecting an image of a mark onto the ground of the eye through said front optical means.

24. An instrument according to claim 22, further comprising a mark projection system for cooperating with said focusing means to project an image of a mark onto the ground of the eye through said front optical means.

25. An instrument according to claim 22, wherein said optical path dividing means includes a dichronic mirror.

26. An instrument according to claim 25, wherein said dichronic mirror reflects infrared radiation.

27. An instrument according to claim 22, wherein said optical path dividing means includes a spot mirror.

28. An instrument according to claim 22, wherein said focusing means focuses the light reflected by the eye ground and incident on said photosensing means.

29. An instrument according to claim 28, wherein said photosensing means is a photosensor array.

* * * * *